US011903983B2

(12) United States Patent
Jimenez Quintana et al.

(10) Patent No.: US 11,903,983 B2
(45) Date of Patent: Feb. 20, 2024

(54) COMPOSITION COMPRISING NEW LACTOBACILLUS SALIVARIUS STRAINS AND METHOD FOR THE PREVENTION AND TREATMENT OF OTITIS AND UPPER RESPIRATORY INFECTIONS

(71) Applicant: PROBISEARCH, S.L.U., Madrid (ES)

(72) Inventors: Esther Antonia Jimenez Quintana, Madrid (ES); Juan Miguel Rodriguez Gomez, Madrid (ES)

(73) Assignee: PROBISEARCH, S.L.U., Madrid (ES)

(*) Notice: Subject to any disclaimer, the term of this patent is extended or adjusted under 35 U.S.C. 154(b) by 0 days.

(21) Appl. No.: 17/808,678

(22) Filed: Jun. 24, 2022

(65) Prior Publication Data

US 2022/0347240 A1 Nov. 3, 2022

Related U.S. Application Data

(62) Division of application No. 16/964,006, filed as application No. PCT/EP2019/051858 on Jan. 25, 2019, now Pat. No. 11,406,674.

(30) Foreign Application Priority Data

Jan. 26, 2018 (EP) ..................................... 18382046

(51) Int. Cl.
| | |
|---|---|
| A61K 39/02 | (2006.01) |
| A61K 35/747 | (2015.01) |
| A23L 33/135 | (2016.01) |
| A61P 31/04 | (2006.01) |
| A61K 9/00 | (2006.01) |
| C12N 1/20 | (2006.01) |

(52) U.S. Cl.
CPC .......... *A61K 35/747* (2013.01); *A23L 33/135* (2016.08); *A61K 9/0053* (2013.01); *A61P 31/04* (2018.01); *C12N 1/20* (2013.01); *A23V 2002/00* (2013.01); *A23V 2400/181* (2023.08)

(58) Field of Classification Search
None
See application file for complete search history.

(56) References Cited

U.S. PATENT DOCUMENTS

| 7,186,545 B2 | 3/2007 | Collins et al. |
| 2003/0091549 A1 | 5/2003 | Collins et al. |
| 2003/0157079 A1 | 8/2003 | Kato et al. |
| 2003/0166257 A1 | 9/2003 | Collins et al. |
| 2013/0309212 A1 | 11/2013 | Zhang et al. |
| 2016/0310407 A1* | 10/2016 | O'Malley ......... B05C 17/00569 |
| 2017/0027997 A1 | 2/2017 | Martin et al. |

FOREIGN PATENT DOCUMENTS

| CN | 104095224 A | 10/2014 |
| KR | 1020110009516 A | 1/2011 |
| RU | 2302458 C2 | 7/2007 |
| WO | 0078322 A1 | 12/2000 |
| WO | 2006007526 A1 | 1/2006 |
| WO | 2007144334 A1 | 12/2007 |
| WO | 2015093937 A1 | 6/2015 |
| WO | 2016077190 A1 | 5/2016 |

OTHER PUBLICATIONS

Janda et al (J.Clin. Microbio. Sep. 2007. 45(9):2761-2764).*
Robert Cohen, MD, et al.., "Probiotics and Prebiotics in Preventing Episodes of Acute Otitis Media in High-Risk . . . ", The Pediatric Infectious Disease Journal, vol. 32, No. 8, pp. 810-814, (2013).
Sara Bover-Cid, et al., "Improved Screening Procedure for Biogenic Amine Production By Lactic Acid Bacteria", International Journal of Food Microbiology, vol. 53, pp. 33-41, 1999.
Itzhak Brook, et al., "In Vitro Bacterial Interference in the Nasopharynx of Otitis Media-Prone and Non-Otitis Media-Prone Children", Arch Otolaryngol Head Neck Surg, vol. 126, pp. 1011-1013, 2000.
Osman Cataloluk, "Molecular Characterization of the Gene Encoding for the Salivaricin B Activity and Its Flanking Sequences", Turk J Biol, vol. 25, pp. 379-386, 2001.
Marie-Helene Coconnier, et al., "Protein-Mediated Adhesion of Lactobacillus Acidophilus BG2FO4 On Human Enterocyte and Mucus-Secreting Cell Lines in Culture", Applied and Environmental Microbiology, vol. 58, No. 6, pp. 2034-2039, 1992.
Paul S. Cohen, et al., "Bacterial Adhesion To and Penetration of Intestinal Mucus in Vitro", Methods in Enzymology, vol. 253, pp. 309-314.
P.L. Conway, et al., "Survival of Lactic Acid Bacteria in the Human Stomach and Adhesion To Intestinal Cells", Journal of Dairy Science, vol. 70, pp. 1-12, 1987.
F. Del Castillo Martin, et al., "Documento De Consenso Sobre Etiologia, Diagnostico Y Tratamiento De La Otitis Media Aguda", Rev Pediatr Aten Primaria, vol. 14, pp. 195-205, 2012.
EFSA, "Guidance On the Assessment of Bacterial Susceptibility To Antimicrobials of Human and Veterinary Importance", EFSA Panel on Additives and Products or Substances used in Animal Feed (FEEDAP). EFSA Journal, vol. 10, No. 6, 2740, pp. 1-10, 2012.
Sarah Flynn, et al., "Characterization of the Genetic Locus Responsible for the Production of ABP-118, a Novel Bacteriocin Produced By the Probiotic Bacterium *Lactobacillus salivarius* Subsp. Salivarius UCC118", Microbiology, vol. 148, pp. 973-984, 2002.
Katja HATAKKA, et al., "Treatment of Acute Otitis Media With Probiotics in Otitis-Prone Children—A Double-Blind, Placebo-Controlled Randomised Study", Clinical Nutrition, vol. 26, pp. 314-321, 2007.
J. Owen Hendley, M.D., "Otitis Media", Clinical Practice, N Engl. J Med, vol. 47, No. 15, pp. 1169-1174, 2002.
M. Juarez Del Valle, "Riboflavin Producing Lactic Acid Bacteria as a Biotechnological Strategy To Obtain Bio-Enriched Soymilk", Food Research International, vol. 62, pp. 1015-1019, 2014.

(Continued)

Primary Examiner — Jennifer E Graser
(74) Attorney, Agent, or Firm — LUCAS & MERCANTI, LLP

(57) ABSTRACT

A strain of *Lactobacillus salivarius* as a probiotic product, and its use in the treatment and/or prevention of otitis and upper respiratory infections.

7 Claims, 2 Drawing Sheets

Figure 1:
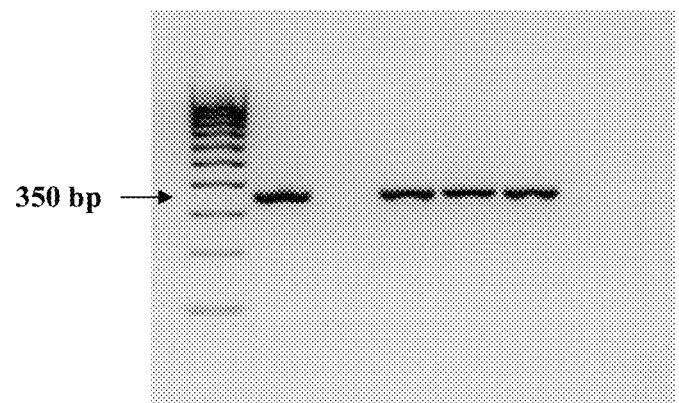

Specification includes a Sequence Listing.

(56) References Cited

OTHER PUBLICATIONS

Ingo Klare, et al., "Evaluation of New Broth Media for Microdilution Antibiotic Susceptibility Testing of Lactobacilli, Pediococci, Lactococci, and Bifidobacteria", Applied and Environmental Microbiology, vol. 71, No. 12, pp. 8982-8986, 2005.

Ingo Klare, et al., "Antimicrobial Susceptibilities of Lactobacillus, Pediococcus and Lactococcus Human Isolates and Cultures Intended for Probiotic or Nutritional Use", Journal of Antimicrobial Chemotherapy, vol. 59, pp. 900-912, 2007.

Jerome O. Klein, "The Burden of Otitis Media", Vaccine, vol. 19, (Suppl 1), pp. S2-S8, 2001.

M.J. Kullen, et al., "Use of DNA Sequence of Variable Regions of the 16S rRNA Gene for Rapid and Accurate Identification of Bacteria in the Lactobacillus Acidophilus Complex", Journal of Applied Microbiology, vol. 89, pp. 511-518, 2000.

Jonathan E. Laino, et al., "Production of Natural Folates By Lactic Acid Bacteria Starter Cultures Isolated From Artisanal Argentinean Yogurts", Canadian Journal of Microbiology, vol. 58, pp. 581-588, 2012.

Susana Langa, et al., "Characterization of Lactobacillus Salivarius Cect 5713, A Strain Isolated From Human Milk: From Genotype To Phenotype", Appl Microbiol Biotechnol, vol. 94, pp. 1279-1287, 2012.

L. Lu, et al., "Generation of DC From Mouse Spleen Cell Cultures in Response To GM-CSF: Immunophenotypic and Functional Analyses", Immunology, vol. 84, pp. 127-134, 1995.

Jesper Magnusson, et al., "*Lactobacillus coryniformis* Subsp. Coryniformis Strain Si3 Produces a Broad-Spectrum Proteinaceous Antifungal Compound", Applied and Environmental Microbiology, vol. 67, No. 1, pp. 1-5, 2001.

P. Marteau, et al., "Survival of Lactic Acid Bacteria in a Dynamic Model of the Stomach and Small Intestine: Validation and the Effects of Bile", Journal of Dairy Science, vol. 80, pp. 1031-1037, 1997.

R. Martin, et al., "Characterization of a Reuterin-Producing Lactobacillus Coryniformis Strain Isolated From a Goat's Milk Cheese", International Journal of Food Microbiology, vol. 104, pp. 267-277, 2005.

R. Martin, et al., "Lactobacillus Salivarius Cect 5713, A Potential Probiotic Strain Isolated From Infant Feces and Breast Milk of a Mother-Child Pair", International Journal Food Microbiology, vol. 112, pp. 35-43, 2006.

Leena Niittynen, et al., "Probiotics and Otitis Media in Children", International Journal of Pediatric Otorhinolaryngol, vol. 76, pp. 465-470, 2012.

Michael E. Pichichero, MD, "Recurrent and Persistent Otitis Media", Pediatr Infect Dis J, vol. 19, pp. 911-916, 2000.

M. Popova, et al., "Beneficial Effects of Probiotics in Upper Respiratory Tract Infections and Their Mechanical Actions To Antagonize Pathogens", Journal of Applied Microbiology, vol. 113, pp. 1305-1318, 2012.

Gregor Reid, et al., "Coaggregation of Urogenital Bacterial in Vitro and in Vivo", Current Microbiology, vol. 20, pp. 47-52, 1990.

Jose Luis Ruiz-Barba, et al., "Small-Scale Total DNA Extraction From Bacteria and Yeast for PCR Applications", Analytical Biochemistry, vol. 347, pp. 333-335, 2005.

J. G. H. Ruseler-Van Embden, et al., "Inability of Lactobacillus Casei Strain GG, L. Acidophilus and Bifidobacterium Bifidum To Degrade Intestinal Mucus Glycoproteins", Scandinavian Journal of Gastroenterology, vol. 30, pp. 675-680, 1995.

E. Stackebrandt, et al., "Taxonomic Note: A Place for DNA-DNA Reassociation and 16S rRNA Sequence Analysis in the Present Species Definition in Bacteriology", International Journal of Systematic Bacteriology, vol. 44, No. 4, pp. 846-849, 1994.

Laura Tapiovaara, et al., "Lactobacillus Rhamnosus GG in the Middle Ear After Randomized, Double-Blind, Placebo-Controlled Oral Administration", International Journal of Pediatric Otorhinolaryngology, vol. 78, pp. 1637-1641, 2014.

P. S. Yap, et al., "Comparison of Newly Isolated Strains of *Lactobacillus delbrueckii* Susp. Lactis for Hydrogen Peroxide Production At 5° C.", J. Dairy Sci., vol. 83, pp. 628-632, 2000.

Jessica A. Younes, et al., "Adhesion Forces and Coaggregation Between Vaginal Staphylococci and Lactobacilli", PLoS One, vol. 7, No. 5, e36917, pp. 1-8, 2012.

J.S.. Zhou, et al., "Potential Probiotic Lactic Acid Bacteria Lactobacillus Rhamnosus (HN001), Lactobacillus Acidophilus (HN017) and Bifidobacterium Lactis (HN019) Do Not Degrade Gastric Mucin in Vitro", International Journal of Food Microbiology, vol. 63, pp. 81-90, 2001.

International Search Report and Written Opinion for Corresponding International Application No. PCT/EP2019/051858 (14 Pages) (dated May 6, 2019).

International Preliminary Report on Patentability for Corresponding International Application No. PCT/EP2019/051858 (9 Pages) (dated Apr. 9, 2020).

Felipe Fredes C, et al., "Uso De Probioticos En Otorrinolaringologia", Rev. Otorrinolaringol. Cir. Cabeza Cuello, vol. 77, pp. 219-227, 2017.

Colombian Search Report corresponding to NC2020/009424 dated Jan. 6, 2022, 2 pages.

Michael Gleeson, et al., "Effects of a Lactobacillus Salivarius Probiotic Intervention On Infection, Cold Symptom Duration and Severity, and Mucosal Immunity in Endurance Athletes", International Journal of Sport Nutrition and Exercise Metabolism, vol. 22, pp. 235-242, 2012.

Ryan Bentley, "L. Salivarius—A Common Probiotic Strain", Blog, Probiotic Education, Product Information; https://humarian.com/l-salivarius/), pp. 1-7, 2017.

* cited by examiner

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Primer pbl16

<400> SEQUENCE: 1
agagtttgat cctggctcag                                              20

<210> SEQ ID NO 2
<211> LENGTH: 20
<212> TYPE: DNA
<213> ORGANISM: Artificial Sequence
<220> FEATURE:
<223> OTHER INFORMATION: Primer mlbl16

<400> SEQUENCE: 2
ggctgctggc acgtagttag                                              20

<210> SEQ ID NO 3
<211> LENGTH: 29
<212> TYPE: DNA
<213> ORGANISM: Artificial Sequence
<220> FEATURE:
<223> OTHER INFORMATION: Primer SalB-for

<400> SEQUENCE: 3
tgataagaaa gaattggcac atataattg                                    29

<210> SEQ ID NO 4
<211> LENGTH: 32
<212> TYPE: DNA
<213> ORGANISM: Artificial Sequence
<220> FEATURE:
<223> OTHER INFORMATION: Primer SalB-rev

<400> SEQUENCE: 4
tctgtttaac tacaaatatt ttgatttgaa tg                                32

<210> SEQ ID NO 5
<211> LENGTH: 23
<212> TYPE: DNA
<213> ORGANISM: Artificial Sequence
<220> FEATURE:
<223> OTHER INFORMATION: Primer Abp118A-for

<400> SEQUENCE: 5
aaacgtggtc ctaactgtgt agg                                          23

<210> SEQ ID NO 6
<211> LENGTH: 24
<212> TYPE: DNA
<213> ORGANISM: Artificial Sequence
<220> FEATURE:
```

```
<223> OTHER INFORMATION: Primer Abp118B-rev

<400> SEQUENCE: 6
aacggcaact tgtaaaacca ccag                                              24
```

COMPOSITION COMPRISING NEW *LACTOBACILLUS SALIVARIUS* STRAINS AND METHOD FOR THE PREVENTION AND TREATMENT OF OTITIS AND UPPER RESPIRATORY INFECTIONS

CROSS REFERENCE TO RELATED APPLICATION

This is a divisional of U.S. application Ser. No. 16/964,006 filed on Jul. 22, 2020, which was a 371 of PCT/EP2019/051858 filed on Jan. 25, 2019 which, in turn, claimed the priority of European Patent Application No. 18382046.3 filed on Jan. 26, 2018, the priority of each of these applications is claimed and each of these applications are incorporated herein by reference.

FIELD OF THE INVENTION

The invention relates to the field of probiotic strains, in particular to a new probiotic strains of *Lactobacillus salivarius*, to compositions comprising it, its obtention and its use for the prevention and treatment of diseases, in particular otitis and upper respiratory infections.

BACKGROUND OF THE INVENTION

Acute otitis media (AOM) is one of the most common bacterial infections and the main reason for antibiotic treatment in childhood (Hendley, 2002). The Eustachian tube is shorter in children than adults which allow easy entry of bacteria and viruses into the middle ear, resulting in acute otitis media. Bacteria such as *Streptococcus pneumoniae* (strep) and *Hemophilus influenzae* (*H. flu*) account for about 85% of cases of acute otitis media and viruses the remaining 15%. Approximately 70% of children experience at least one otitis episode by the age of 2 years, and 20-30% suffer from recurrent AOM (Pichichero, 2000). Recurrent AOM (rAOM) causes discomfort in the children and their families, and poses an economic burden on society (Klein, 2001).

Upper respiratory infections (URI), also known as the common cold, is one of the most common illnesses, leading to more health care provider visits and absences from school and work than any other illness every year. Most children younger than 2 years experience several URIs during the first year of life, and one-quarter suffer from recurrent or prolonged infections in developed countries. Caused by a virus that inflames the membranes in the lining of the nose and throat, colds can be the result of more than 200 different viruses. However, among all of the cold viruses, the rhinoviruses cause the majority of colds. Other virus types include coronavirus, parainfluenza, adenovirus, enterovirus, and respiratory syncytial virus. The viruses cause an immune reaction. This, in turn, causes increase in mucus production, swelling of the lining of the nose, making it hard to breath and causing congestion, sneezing and cough from the increased mucus dripping down the throat. Upper respiratory infections are also a prominent risk factor for acute otitis media.

URIs lead to inappropriate prescription of antibiotics in pediatric practice because antibiotics are not effective against viruses. Inappropriate and wide use of antibiotics may lead to the development of bacterial resistance and disturb the normal balance of human microbiota, facilitating the pathogen colonization and reducing availability of vaccines for viruses.

Similarly, antibiotic treatment and prophylaxis against the recurrence of AOM inevitably lead to the development of antibiotic-resistant microorganisms and disturbances in the balance of the normal upper respiratory tract microbiota, which further facilitate the colonization of pathogens (Brook and Gober, 2000).

Probiotics are defined by the World Health Organization as live microorganisms that, when administered in adequate amounts, confer a health benefit on the host. The most commonly used probiotics are *Lactobacillus* and *Bifidobacterium* species, followed by the genera *Streptococcus, Enterococcus, Propionibacterium, Bacillus*, and *Escherichia coli*. In addition, some yeast species are used as probiotics, for example, *Saccharomyces boulardii* and *Saccharomyces cerevisiae* are frequently used to treat gastrointestinal disorders. Probiotic products may be formulated as capsules, tablets, powders (which are regulated as a dietary supplement), and a food ingredient (e.g., yogurts, kefirs), or as a drug. Probiotics may exert a wide range of beneficial effects, such as balancing the host gut microbiota and interacting with the innate and adaptive immune system, which may promote resistance against pathogens.

In the past few years, probiotics have been widely used in health conditions of respiratory, gastrointestinal, and urogenital tract infections, allergies, necrotizing enterocolitis in preterm infants, infantile colic, autoimmune diseases, and irritable bowel syndrome (IBS). Probiotic therapies offer an attractive option for re-establishing the microbial equilibrium and preventing infectious diseases, including otitis (Niittynen et al., 2012). The mechanisms of probiotics that contribute to microbial interference with pathogens may include competition for essential nutrients and adhesion sites on the epithelial surface, the production of bacteriocins and other inhibitory substances, and the enhancement of mucosal and systemic immunity (Popova et al., 2012).

WO2006/007526 describes a method for treating or preventing respiratory infections and acute otitis media in infants, comprising the administration of a Bifidobacteria strain and an adherence promoting probiotic such as a *Lactobacillus* species.

WO2016/0077190 describes the use of *Lactobacillus* species in a composition for respiratory administration to prevent the pathogenic inflammatory sequelae of respiratory virus infections.

WO2015/093937 describes the use of a strain of *Lactobacillus salivarius* for the treatment of mastitis.

Otitis, in particular Acute Otitis Media (AOM), and Upper Respiratory Infection (URI) are a widespread health problem among small children, and preventive and treatment strategies are urgently needed. Previous studies have shown that probiotics reduces the occurrence of URIs and AOM in healthy children but the same strains have failed to prevent such conditions or to reduce nasopharyngeal carriage of causal pathogens in highly otitis-prone children. Therefore, there is a need for new treatments of otitis and upper respiratory infections, particularly in otitis-prone children.

BRIEF DESCRIPTION OF THE INVENTION

We have isolated and characterized a probiotic strain of *Lactobacillus salivarius* isolated from a vaginal swab of a healthy women useful for the prevention and/or treatment of otitis and other conditions of the upper respiratory tract, such as upper respiratory infections. As shown in the examples, the *Lactobacillus salivarius* PS7 strain of the invention is able to reduce the occurrence of acute otitis media (AOM) episodes in children suffering from recurrent AOM (otitis-prone children) and/or the external auditory canal carriage of otitis pathogens, showing a high potential for prevention in such highly predisposed population. The *Lactobacillus salivarius* strain PS7 has been deposited and has been given accession number CECT9422.

*Lactobacillus salivarius* strain PS7 of the invention, accession number CECT 9422, was deposited on 18 Jul. 2017 at the international depositary authority Colección Española de Cultivos Tipo (CECT) with the address at Edicicio 3 CUE, Parc Cientific Universitat de Valencia, Catedrático Agustín Escardino, 9, Paterna (Valencia), Spain 46980.

In one aspect, the present invention is directed to a strain of *Lactobacillus salivarius* PS7 or a strain having at least 95% identity with this strain, or mutant strains thereof, wherein the mutant strains are obtained by using the deposited strain as starter material, and wherein the mutant strains retain or further improve the activity of the strain *Lactobacillus salivarius* PS7 in the treatment of prevention of otitis and upper respiratory infections. Preferably the strain has at least 97% identity with the strain of *Lactobacillus salivarius* PS7.

In another aspect, the strain is *Lactobacillus salivarius* PS7.

The invention is also directed to a composition comprising a strain as defined above, and its use as a probiotic.

In another aspect, the invention is directed to the strains or composition as defined above for the prevention and/or treatment of Otitis or Upper Respiratory Infections (URI), preferably in the treatment and/or prevention of Acute Otitis Media (AOM).

The strains and compositions of the invention are especially useful for the treatment and/or prevention of Otitis or Upper Respiratory Infections in otitis-prone children.

In another aspect, the invention is directed to pharmaceutical products comprising an effective amount of the strains as previously defined, together with pharmaceutically acceptable excipients.

In another aspect, the invention is directed to an edible product comprising an effective amount of the strain as defined above, together with other edible ingredients. Preferably, the edible product is selected from a dietary supplement, a nutraceutical or a dairy product.

FIGURES

FIG. 1.—PCR assay for the detection of the structural gene of the bacteriocin Abp118. Lane 1: marker (Hyperladder™ 100 bp, BIOLINE). Lane 2: positive control. Lane 3: negative control. Lanes 4, 5 and 6: *L. salivarius* PS7.

Figure 2:
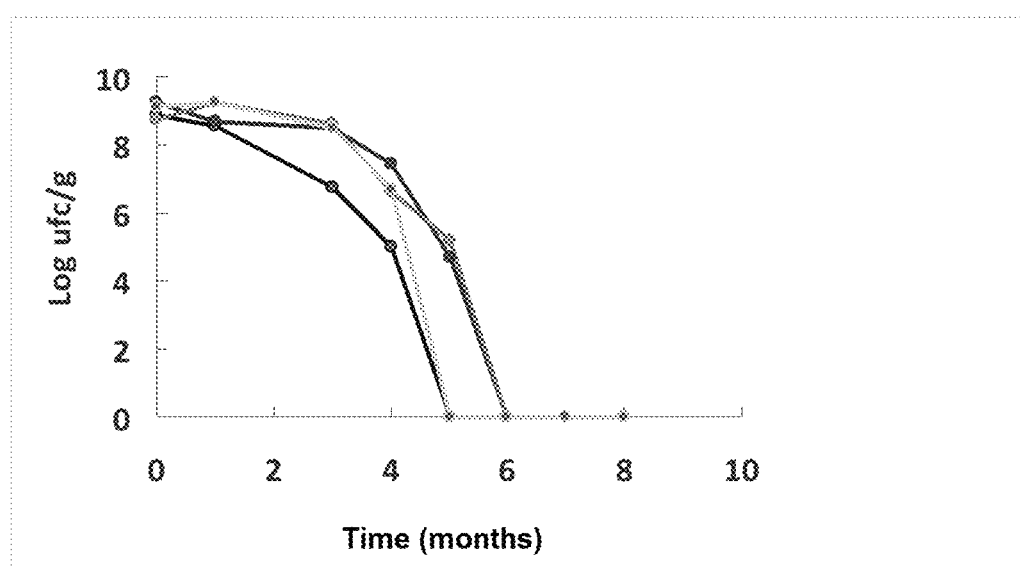

FIG. 2.—Stability of freeze-dried *L. salivarius* PS7 cultures (red line) when stored at room temperature.

Figure 3:
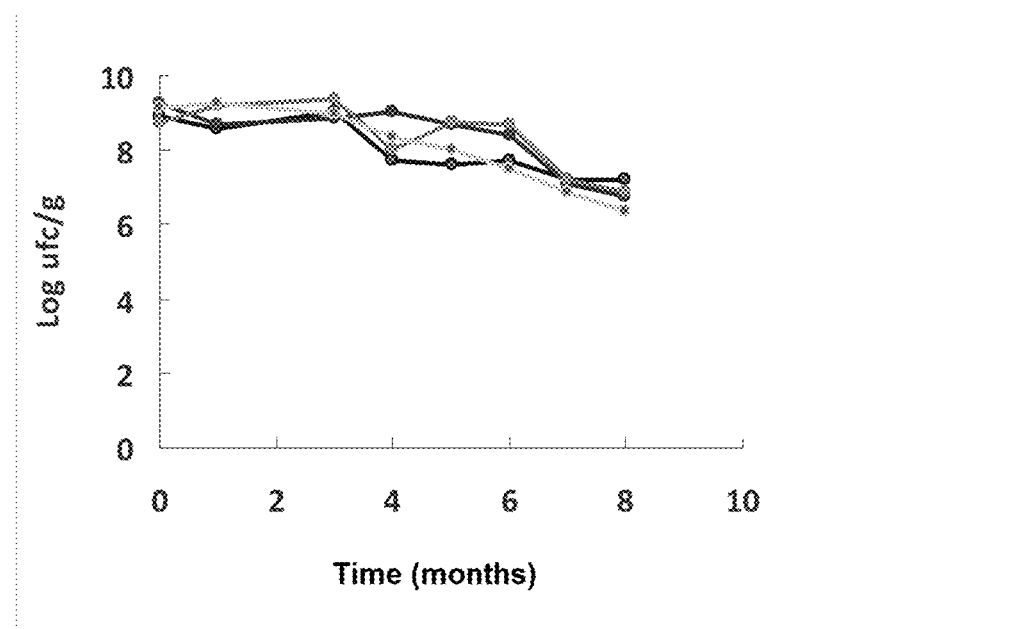

FIG. 3.—Stability of freeze-dried *L. salivarius* PS7 cultures when stored at 4° C.

DETAILED DESCRIPTION OF THE INVENTION

Definitions

In the present description:

The term "probiotic" means a microorganism that exerts beneficial effects on the health of the host. It can be a live microbial fed supplement or medicament that beneficially affects the host by improving its microbial balance, a microbial preparation that contains live or dead bacteria, or a combination of both.

The term "strain" is well-known in the field and means a genetic variant or subtype of a microorganism. A "mutant Strain" is that is different from the wild type by one or more (new) characteristics as caused by mutation(s).

The term "Otitis" means inflammation of the ear. In the case of Otitis Media there is inflammation of the middle ear characterized by the accumulation of infected fluid in the middle ear, bulging of the eardrum, pain in the ear and, if eardrum is perforated, drainage of purulent material (pus) into the ear canal.

The term "Upper Respiratory Infection" means an infection of the upper part of the respiratory system which is above the lungs. An upper respiratory infection can be due to any number of viral or bacterial infections. These infections may affect the throat (pharyngitis), nasopharynx (nasopharyngitis), sinuses (sinusitis), larynx (laryngitis), trachea (tracheitis) or bronchi (bronchitis).

The term "effective amount" as used herein, means an amount of an active agent high enough to deliver the desired benefit, but low enough to avoid serious side effects.

Probiotic Strain PS7

The strain of *Lactobacillus salivarius* according to the invention is referred to as *Lactobacillus salivarius* PS7 or *L. salivarius* PS7. The strain *L. salivarius* PS7 has been deposited by Probisearch SLU, Calle Santiago Grisolía 2, Tres Cantos, Spain in accordance with the Budapest Treaty on the International Recognition of the Deposit of Microorganisms for the Purpose of Patent Procedure at the Colección Española de Cultivos Tipo (CECT) on 18 Jul. 2017 and has been given Accession Number CECT9422.

The present invention also relates to strains of *L. salivarius* having at least 95% identity with the 16S rRNA sequence of the *L. salivarius* PS7 strain which is described in the examples (reference Stackebrandt & Goebel, 1994: "Taxonomic Note: A Place for DNA-DNA Reassociation and 16s rRNA Sequence Analysis in the Present Species Definition in Bacteriology" Int. J. Syst. Bacteriol. 44:846-849).

In a preferred embodiment, the strain according to the present invention has at least 97% identity with the 16S rRNA sequence of the *L. salivarius* PS7 strain, more preferably at least 98% identity, more preferably at least 99% identity. In another preferred embodiment, the strain according to the present invention has 100% identity with the 16S rRNA sequence of the *L. salivarius* PS7, i.e. the strain according to the present invention is the *Lactobacillus salivarius* strain PS7.

From the deposited *Lactobacillus salivarius* PS7 strain, the person skilled in the art can routinely, by conventional mutagenesis or re-isolation techniques, obtain further mutants or derivatives thereof that retain the herein described relevant features and advantages of the PS7 strain. Therefore, mutant strains of *Lactobacillus salivarius* PS7 are also part of the invention. In the context of the present invention, the term "a mutant thereof" relates to mutant strains obtained by using the deposited strains as starting material, said mutant strains retaining or enhancing the therapeutic properties of the parent strains. The person skilled in the art will decide upon the adequate method to be employed for determining the therapeutic activity of the strains, in particular the treatment and/or prevention of Otitis and Upper Respiratory infections, such as those described in the examples of the present application.

The strains of the invention, as demonstrated in the examples, are highly resistant to the conditions of the gastrointestinal environment of mammals (acidic environment, high lysozyme, bile salt and oxygen peroxide concentrations), thus being able to survive passage through the GIT. The strains also have good adhesion to the intestinal epithelium, which allows them to remain in the intestinal tract and to exert their probiotic effects.

In the present invention live microorganisms as defined above are preferred, as they produce a complete array of antigens, reproduce to increase the number of such organisms in the intestinal environment or other body tissues to promote mucosal interaction, and may adhere to the intestinal or other body tissues to better stimulate a mucosal immune response.

Composition

Preferably, the strain of *L. salivarius* PS7 of the invention, or mutant strains thereof, is comprised in a composition, such as a nutritional composition, a nutritional supplement, a pharmaceutical composition or a nutraceutical composition, preferably a nutritional composition or a nutritional supplement, or a medicament. Preferably, the composition of the invention comprises the strain of *L. salivarius* PS7 of the invention or mutant strains thereof and a physiologically acceptable carrier or excipient and/or further ingredients as described further below. Preferably, the strain of *L. salivarius* according to the invention is present in freeze-dried form.

Any physiologically acceptable excipient or carrier as known in the art may be used. Suitable excipients or carriers include, but are not limited to, water, glucose, lactose, sucrose, mannitol, maltodextrin, (resistant) starch, cellulose or cellulose derivatives, e.g. methylcellulose, magnesium stearate, stearic acid, sodium saccharin, talcum, magnesium carbonate and the like.

The composition according to the invention may comprise further probiotics, apart from the strain of *L. salivarius* PS7 or mutant strains thereof as described above. Probiotics have beneficial effects on the immune system, hence the combination with probiotics will have a superior effect on immune system. Preferably, the further probiotics are selected from the group consisting of *Lactobacillus* and *Bifidobacterium*.

The composition of the present invention may further contain prebiotics. Prebiotics may support the growth of probiotics before they are rendered non-replicating. "Prebiotic" means non-digestible food substances that promote the growth of health beneficial micro-organisms and/or probiotics in the intestines. They are not broken down in the stomach and/or upper intestine or absorbed in the GI tract of the person ingesting them, but they are fermented by the gastrointestinal microbiota and/or by probiotics. Preferably, they may be selected from the group consisting of oligosaccharides, optionally containing fructose, galactose, mannose; dietary fibers, in particular soluble fibers, soy fibers; inulin; or mixtures thereof. Preferred prebiotics are fructo-oligosaccharides, galacto-oligosaccharides, isomalto-oligosaccharides, xylo-oligosaccharides, arabino-xylo oligosaccharides, mannan-oligosaccharides, oligosaccharides of soy, glycosylsucrose, lactosucrose, lactulose, palatinose-oligosaccharides, malto-oligosaccharides, gums and/or hydrolysates thereof, pectins and/or hydrolysates thereof.

The effective amount of colony forming units (cfu) for each strain in the composition of the invention will be determined by the skilled person and will depend upon the final formulation. For instance, in edible products, the strain of the invention is present in an amount from about $10^5$ cfu/g to about $10^{12}$ cfu/g, preferably in an amount from about $10^7$ cfu/g to about $10^{12}$ cfu/g, more preferably in an amount from about $10^9$ cfu/g to about $10^{12}$ cfu/g. All amounts are expressed as grams dry weight.

The term CFU refers to "Colony Forming Units". Quantification of bacteria in a given sample is routinely achieved by counting the total number of colony-forming units (CFUs) grown on an agar plate from serial dilutions, expressed as CFU per gram or mL of the original sample. This yields an estimate of the number of cells present based on a skilled interpretation of the number of colonies on a plate.

In a preferred embodiment, the composition according to the invention is a nutritional composition or a nutritional supplement. The supplement according to the invention may be in the form of a powder, a tablet (including chewable table) or a capsule. The nutritional composition according to the invention may be any food product or beverage. Preferably, the composition, especially the nutritional supplement, according to the invention further comprises a physiologically acceptable excipient or carrier. In a preferred embodiment, the composition or the supplement is a powder, packed in container (preferably a sachet) comprising 1 to 10 g, more preferably 1.5 to 7 g, most preferably 2 to 5 g. Preferably, each container contains a single dose.

If the composition according to the invention is used as a dietary supplement, it can be administered as such, can be mixed with a suitable drinkable liquid, such as water, yoghurt, milk or fruit juice, or can be mixed with solid or liquid food. In this context the dietary supplement can be in the form of tablets, pills, capsules, granules, powders, suspensions, sachets, pastilles, sweets, bars, syrups and corresponding administration forms, usually in the form of a unit dose.

Mode of Administration

The composition used in the present method is preferably administered enterally, more preferably orally. The composition according to the invention may be administered in a single daily dose or multiple doses per day, such as at least 2 doses per day, at least 3 doses per day, at least 4 doses per day. Preferably, the composition according to the invention is administered more than once per day. In an especially preferred embodiment, the composition according to the invention is administered in 2 or 3 doses per day, most preferably in 3 doses per day. Preferably the strain of the invention or mutants thereof is administered in an amount of $10^5$ cfu/dose to about $10^{12}$ cfu/dose, preferably in an amount from about $10^7$ cfu/dose to about $10^{12}$ cfu/dose, more preferably in an amount from about $10^9$ cfu/dose to about $10^{12}$ cfu/dose. By the term "per dose" it is meant that this amount of microorganism is provided to a subject either per day or per intake, preferably per day. The person skilled in the art will be able to adjust the therapeutically effective dose and/or the prophylactic effective dose appropriately.

In prophylactic applications, compositions according to the invention are administered to a person susceptible to or otherwise at risk of a disorder in an amount that is sufficient to at least partially reduce the risk of developing that disorder. Such an amount is defined to be "a prophylactic effective dose". Again, the precise amounts depend on a number of factors such as the child's state of health and weight, and on the effect of the food matrix.

In an embodiment of the invention the strain or composition of the invention is administered to a child. In a preferred embodiment, the child is of preschool age. In some preferred embodiments, the child is between the ages of about 3 years and about 5 years.

In an embodiment, the child is an otitis-prone child. Preferably the child suffers or is susceptible to suffer from Otitis and/or Upper Respiratory Infections.

Beneficial Effects

As evidenced by the examples below, the strains and compositions of the invention are safe and have an important beneficial effect. In a clinical study, the strains of the invention decreased in 86% the number of AOM episodes during a 6 month intervention of otitis-prone children as compared with the 6 months period before the intervention. It also reduced the median duration of AOM episodes when AOM occurred. Finally, the strains of the invention reduced the number of episodes of Upper Respiratory Infections in children receiving the probiotic.

EXAMPLES

Example 1: Identification and Characterization of the Strain PS7

1.1. Isolation from Vaginal Swab and Identification (Species and Strain)

*Lactobacillus salivarius* PS7 was isolated in the frame of a study to evaluate the bacterial diversity of the *Lactobacillus* group in human milk and the vagina of healthy women and understand their potential translocation from the gut. Women were enrolled in this study according with the following criteria: (a) healthy women without present or past underlying conditions (including mastitis); (b) normal full-term pregnancy; and (c) absence of infant and/or maternal perinatal problems (including mastitis). Milk samples, vaginal swabs and rectal swabs were aseptically collected in sterile tubes and swabs. at day 7 after delivery and kept at 4° C. until delivery to the laboratory, which happened within the first three hours after collection. The study from which this strain was isolated was approved by the Ethical Committee on Clinical Research of Hospital Clínico (Madrid).

The biological material contained in the vaginal and rectal swabs was resuspended in 1 ml of peptone water. Dilutions of the samples with peptone water were plated in triplicate onto de Man, Rogosa, and Sharpe (MRS, Oxoid, Basingstoke, UK) supplemented with L-cysteine (0.5 g/L) (MRS-Cys) agar plates, which were incubated anaerobically (85% nitrogen, 10% hydrogen, 5% carbon dioxide) in an anaerobic workstation (MINI-MACS, DW Scientific, Shipley, UK) at 37° C. for 48 h.

The isolates were examined by phase-contrast microscopy to determine cell morphology and Gram-staining reaction, and tested for oxidase and catalase activities and, also, for good growth (>$10^8$ CFU/ml) in MRS broth incubated at 37° C. for up to 24 h.

The strain was isolated from a vaginal swab and identified at the species level as *Lactobacillus salivarius* by PCR amplification of a section of a 16S rRNA gene variable region using primers pb116 (5'-AGAGTTT-GATCCTGGCTCAG-3', SEQ ID NO: 1) and mb116 (5'-GGCTGCTGGCACGTAGTTAG-3', SEQ ID NO: 2) (Kullen et al. 2000). PCR conditions were as follows: 96° C. for 30 s, 50° C. for 30 s and 72° C. for 45 s (35 cycles) and a final extension at 72° C. for 4 min. Amplified fragments were purified using the NucleoSpin Extract II (Macherey-Nagel Gmb; Duren, Germany) and sequenced using the primers cited above on an ABI 377A automated sequencer (Applied Biosystems, Foster City, USA). The sequences were compared with those deposited in the EMBL database using BLAST algorithm (http://www.ncbi.nlm.nih.gov/BLAST).

The identification was confirmed by Matrix Assisted Laser Desorption Ionization-Time of Flight (MALDI-TOF) mass spectrometry using a Vitek-MS™ instrument (BioMérieux, Marcy l'Etoile, France) in the facilities of Probisearch (Tres Cantos, Spain). Briefly, a portion of a bacterial colony (~1 μL) was directly spotted onto a MALDI sample plate. Then, it was overlaid with 1 μL of a saturated solution of α-cyano-4-hydroxycinnamic acid in acetonitrile (28%), and allowed to dry at room temperature. A mean spectrum was constructed with at least 50 m/z spectra profiles and used for the identification by comparison with the spectra contained in the Myla database (Biomerieux). Identification was defined as a 99-100% match to the species-specific m/z values in the database.

The strain could be differentiated from other *L. salivarius* strains of our own collection by genotyping by randomly amplified polymorphic DNA (RAPD) and pulsed-field gel electrophoresis (PFGE) analyses.

1.2. Survival after Transit Through an In Vitro Gastrointestinal Model

The survival of the strain was tested in an in vitro model of the human stomach and small intestine based on that described by Marteau et al. (1997). UHT-treated human milk (25 ml) containing approximately $10^9$ CFU/ml of the strain tested was diluted in 5 ml of a sterile electrolyte solution containing 6.2 g/l of NaCl, 2.2 g/l of KCl, 0.22 g/l of CaCl$_2$, and 1.2 g/l of NaHCO$_3$ to simulate the in vivo dilution by saliva. Then, 5 ml of porcine gastric juice was added and the mixture was incubated at 37° C. with agitation. The pH curve in the stomach-resembling compartment was controlled to reproduce the values found in monogastrics after yogurt consumption (Conway et al. 1987): pH 5.0 at initiation, pH 4.1 at 20 min, pH 3.0 at 40 min, and pH 2.1 at 60 min. Fractions were successively taken from this compartment at 20, 40, 60, and 80 min, in a manner that simulates the normal gastric emptying (Marteau et al. 1997). After adjusting their pH to 6.5±0.2 with 1 M NaHCO$_3$, they were mixed with 10 ml of a sterile electrolyte solution containing 5 g/l of NaCl, 0.6 g/l of KCl, 0.3 g/l of CaCl$_2$, 4% of porcine bile, and 7% of pancreatin (Sigma), which simulates the content of the duodenal juice. After 120 min of successive exposure to these conditions, bacterial survival was determined by plating the samples onto MRS agar plates, which were anaerobically incubated at 37° C. for 48 h. All these assays were performed in quadruplicate and the values were expressed as the mean±SD.

Results: the viability of the strain after exposition to conditions simulating those found in the gastrointestinal tract was high (51.53%; Table 1).

TABLE 1

Percentage (%) of the cells inoculated ($10^9$ CFU/ml) in milk that survived to conditions simulating those of the human gastrointestinal tract

| Gastric-simulation | | | | |
|---|---|---|---|---|
| 0-20 min (pH 5.0) | 20-40 min (pH 4.1) | 40-60 min (pH 3.0) | 60-80 min (pH 2.1) | % Total |
| 12.11 ± 2.21 | 16.01 ± 2.97 | 16.33 ± 3.03 | 07.08 ± 1.55 | 51.53 |

1.3. Determination of Antimicrobial Spectrum

An overlay method previously described (Magnusson & Schnürer, 2001; Martín et al., 2005; Martín et al., 2006) was used to determine the ability of the strain to inhibit the growth of different bacteria involved in cases of acute otitis media, including several strains (n=55) of the following species: *Haemophilus influenza, Streptococcus pneumoniae, Streptococcus pyogenes, Moraxella catharralis, Alloiococcus otitis, Actinomyces europaeus, Enterococcus faecalis,*

Staphylococcus aureus, Staphylococcus epidermidis, Escherichia coli and Pseudomonas aeruginosa. Some of the strains belonged to our own collection while the rest of the strains were provided by Dr. Patricia Ruiz Garbajosa (Servicio de Microbiología, Hospital Universitario Ramón y Cajal (Madrid). The plates overlaid with bacterial indicators were incubated at 37° C. for 48 h and, then, were examined for zones of inhibition around the strain streaks. All experiments assaying inhibitory activity were performed in triplicate.

L. salivarius PS7 showed a clear inhibitory antimicrobial activity (inhibition zone>2 mm around the streak) against all indicator organisms used in this study.

To elucidate the compound(s) responsible for the antimicrobial activity, the strain was screened for production of bacteriocins, hydrogen peroxide, lactate, and/or acetate.

1.4. Production of Bacteriocins

The strain L. salivarius PS7 was grown in MRS broth at 37° C. until early stationary phase ($A_{620}$~1.0). The culture was centrifuged at 12,000 g for 10 min at 4° C., and the supernatant was neutralized to 6.2 with 1 M NaOH, boiled for 5 min, and filter-sterilized through 0.22 µm-pore-size filters (Millipore, Bedford, USA). The bacteriocinogenic activity of the cell-free supernatants was determined by an agar well diffusion assay. Aliquots (100 µl) of the supernatants were placed in wells (7-mm diameter), cut in cooled BHI agar plates previously seeded ($10^5$ cfu/ml) with the indicator strains. The plates were kept at 4° C. for 2 h, and then incubated under optimal conditions for growth of the indicator. The microorganisms employed as indicators of bacteriocinogenic activity were different bacterial strains of the following species Haemophilus influenza, Streptococcus pneumoniae, Streptococcus pyogenes, Moraxella catharralis, Alloiococcus otitis, Actinomyces europaeus, Enterococcus faecalis, Staphylococcus aureus, Staphylococcus epidermidis, Escherichia coli and Pseudomonas aeruginosa.

Since L. salivarius PS7 showed bacteriocinogenic activity against some of the indicator strains tested in this work, PCR analyses were carried out in order to detect structural genes related to the biosynthesis of salivaricins. Briefly, one colony was resuspended in 50 µl of sterile water; then, 50 µl of chloroform were added to the suspension; the mix was centrifuged at 13,000×g for 10 min at 4° C. Subsequently, 5 µl of the aqueous phase were used as DNA template in the PCR assays using the following primers' couples: (i) SalB-for (5'-TGATAAGAAAGAATTGGCACATATAATTG-3', SEQ ID NO: 3) and SalB-rev (5'-TCTGTTTAACTA-CAAATATTTTGATTTGAATG-3', SEQ ID NO: 4) for salivaricin B (Çataloluk, 2001); (ii) Abp118A-for (5'-AAACGTGGTCCTAACTGTGTAGG-3', SEQ ID NO: 5) and Abp118B-rev (5'-AACGGCAACTTGTAAAAC-CACCAG-3', SEQ ID NO: 6) for bacteriocin Abp-118 (Flynn et al., 2002). Each PCR reaction (20 µl) contained 5 µl of the buffer mix (5× MyTaq Red), 0.5 µl of each primer, 0.15 µl of the enzyme MyTaq Red DNA polymerase (BIOLINE) and 13.85 µl of deionized water. The PCR program was as follows: an initial denaturation step (95° C. for 2 min), followed by 30 cycles of 95° C. for 30 s, 58° C. for 30 s and 72° C. for 30 s, and a final extension of 72° C. for 5 min. The amplicons were visualized by agarose (2%) gel electrophoresis at 90 V for 1 h, using a 100-1,013 bp ladder (Hyperladder™ 100 bp, BIOLINE) and as a marker and Gel Red Nucleic Acid Stain (Biotium) as the staining agent, in a gel imaging system (Gel Doc 2000, Bio-Rad).

The strain displayed a notable bacteriocin activity against the Gram-positive strains included as indicator organisms used in this study. PCR analysis for structural genes of known salivaricins revealed that this strain is able to produce the bacteriocin Abp-118 as shown in Figure. 1.

1.5. Production of Hydrogen Peroxide

Hydrogen peroxide production by the Lactobacillus strain was initially tested following the procedure described by Song et al. (1999). MRS agar plates supplemented with 0.25 mg/ml of tetramethylbenzidine (TMB; Sigma, St. Louis, USA) and 0.01 mg/ml of horseradish peroxidase (HRP, Sigma) were inoculated with the strain and anaerobically incubated for 2 days at 37° C. HRP is known to oxidize TMB in the presence of hydrogen peroxide to form a blue pigment in the $H_2O_2$-producing colony. Parallel, the hydrogen peroxide was also measured by a modification of the quantitative method of Yap and Gilliland (2000). The strain was anaerobically grown in 10 ml of MRS broth for 24 h at 37° C. The cells were harvested by centrifugation at 12000×g for 10 min at 4° C., washed twice with potassium phosphate buffer (50 mM, pH 6) and resuspended in 9 ml of the same buffer supplemented with 5 mM glucose. The cell suspension (0.5 ml) was inoculated into a tube containing 9 ml of the glucose-containing buffer. After an aerobic incubation at 37° C. for 24 h, the cells were removed by centrifugation at 12000×g for 10 min at 4° C., and the supernatants were assayed for hydrogen peroxide. Briefly, 5 ml of supernatant were mixed with 100l of 1% aqueous o-dianisidine (Sigma), and 1 ml of 0.001% aqueous HRP. The tubes were incubated for 10 min at 37° C. and the reaction was stopped by adding 0.2 ml of 4 N HCl. Absorbance reading ($A_{400}$ nm) was determined and peroxide content was quantified by comparing the values obtained with those of a $H_2O_2$ standard curve. In all the $H_2O_2$ assays, L. johnsonii La1 was used as a positive control.

L. salivarius PS7 was positive in a qualitative screening for hydrogen peroxide production; later, a quantitative assay showed that the amount of $H_2O_2$ produced by this strain was 0.729 µg/ml±0.240 while the production of the control strain (L. johnsonii La1) was higher (7.63 µg/mL±0.407).

1.6. Production of Lactic Acid and Acetic Acid

Lactic acid production by the L. salivarius strain was determined in MRS broth (pH 6.2). One percent inoculum's from an overnight MRS culture was used and incubation proceeded for 24 h at 37° C. anaerobically (85% Nitrogen, 10% Hydrogen, 5% Carbon dioxide) in a MACS-MG-1000-anaerobic workstation (DW Scientific, Shipley, UK). Cells were removed by centrifugation at 12000×g for 5 min and the concentration of L- and D-lactic acid in the supernatants was quantified using an enzymatic kit (Roche Diagnostics, Mannheim, Germany), following the manufacturer's instructions. The pH values of the supernatants were also measured. Similarly, the concentration of acetic acid in the culture supernatants was quantified using another enzymatic kit (Roche Diagnostics) and following the manufacturer's instructions. In this case, MRS was constituted from its different ingredients excluding sodium acetate. These assays were performed in triplicate and the values were expressed as the mean±SD.

Results: L. salivarius PS7 produced a high concentration of L-lactic acid while it did not produce the D-lactic acid isomer (Table 2). A significant concentration of acetic acid could also be detected in the culture supernatants of the strain (0.68 mg/mL±0.17).

TABLE 2

Concentration of L- and D-lactic acid (mg/mL; mean ± SD) and pH of the supernatants obtained from MRS cultures of the *lactobacilli* (n = 4).

| Strain | pH | L-lactic acid | D-lactic acid |
|---|---|---|---|
| L. salivarius PS7v | 3.83 | 10.29 ± 0.70 | Nd |
| L. rhamnosus GG | 3.97 | 6.44 ± 0.92 | Nd |
| L. johnsonii La1 | 3.96 | 3.95 ± 0.41 | 7.86 ± 1.36 |
| L. casei imunitass | 4.02 | 7.05 ± 0.64 | Nd |

Nd, not detectable.

Globally, these results show that *L. salivarius* PS7 is a very singular strain with a very high potential to inhibit pathogenic bacteria since it is able to simultaneously produce, at least, four antimicrobial compounds (a bacteriocin, hydrogen peroxide, L-lactate and acetate).

1.7. Coaggregation Assays

The ability of the strain to aggregate with cells of the otitis-related strains cited above was also investigated following the procedure of Reid et al. (1990), adapted by Younes et al. (2012). This assay is based in co-cultures in broth media and optical microscopy techniques.

*L. salivarius* PS7 showed a big potential to coaggregate with bacterial strains involved in otitis media, particularly with those belonging to the genera *Streptococcus, Alloiococcus, Enterococcus* and *Staphylococcus*. This mechanism may prevent the interaction of such pathogens with their human target cells.

1.8. Adhesion to Caco-2/HT-29 Cells

The adherence of the strain to HT-29 and Caco-2 cells was examined basically as described by Coconnier et al. (1992). Routinely, cells were grown in DMEM medium (PAA, Linz, Austria) containing 25 mM glucose, 1 mM sodium pyruvate and supplemented with 10% heat-inactivated (30 min, 56° C.) fetal calf serum, 2 mM L-glutamine, 1% non-essential amino acid preparation, 100 U/mL penicillin and 100 mg/mL streptomycin. For the adherence assays, HT-29 and Caco-2 were cultured to confluence in 2 mL of medium devoid of antibiotics. Approximately 10 days postconfluence, 1 mL of the medium was replaced with 1 mL of *Lactobacillus* suspension ($10^8$ cfu/mL in DMEM). The inoculated cultures were incubated for 1 h at 37° C. in 5% $CO_2$. Then, the monolayer was washed five times with sterile PBS, fixed with methanol, stained with Gram stain and examined microscopically. The adherent lactobacilli in 20 random microscopic fields were counted for each test.

The strain showed a high ability to adhere to Caco-2 cells (697.1±297.6; expressed as the mean±SD of the number of adhered lactobacilli in 20 random microscopic fields), and HT-29 cells (251.7±82.3).

1.9. Production of Riboflavin/Folate/Cianocobalamin

*L. salivarius* PS7 bacterial cells from an overnight culture in MRS were washed 3 times with saline solution, resuspended in this solution at the original culture volume, and used to inoculate (4%; v/v) either riboflavin-, folate- or vitamin B12-free culture media (Difco, USA). Then, the inoculated media were incubated at 37° C. for 18 h without agitation. After incubation, this washing-resuspension procedure was repeated and the resulting cell solution was used to inoculate (2%; v/v) the respective fresh vitamin-free media. This last step was repeated 7 times and, after the last incubation, samples were taken to determine extra- and intra-cellular vitamin concentrations. For determination of folate concentration, a sample (500 µl) of bacterial grown vitamin-free medium was mixed with equal parts of a protecting buffer (0.1 M phosphate buffer, pH 6.8, containing ascorbic acid [1.5%; w/v]) to prevent vitamin oxidation and degradation while acetic acid (1%; v/v) was added in the case of riboflavin. Immediately after the addition of either the protecting buffer or acetic acid, the mixes were centrifugated for 5 min at 5,000×g. Then, the supernatant was collected (extracellular sample) and boiled for 5 min while the pellet was resuspended in 500 µl of protecting buffer, boiled for 5 min, centrifuged for 6 min at 10,000×g and the corresponding supernatant was also collected (intracellular samples). All supernatants were stored at −70° C. until used for vitamin quantification.

Folate concentrations were determined by a previously described microbiological assay using *Lactobacillus rhamnosus* NCIMB 10463 as the indicator organism (Laiño et al. 2012). Briefly, samples or different concentrations of HPLC-grade folic acid (Fluka BioChemica, Sigma-Aldrich, Switzerland) were placed with the indicator strain and incubated statically during 48 h at 37° C. in 96-well sterile microplates containing the folate-free medium (Deltalab, Argentina). The optical density was read at 580 nm ($OD_{580}$) using a microplate reader (VERSAmax tuneable microplate reader, Molecular Devices, USA). The folate concentration of the samples was determined by comparing the OD with those obtained with the standard curve prepared using commercial folic acid. Riboflavin concentrations were determined in the same manner but using *L. rhamnosus* ATCC 7469 as the indicator strain grown in the riboflavin-free medium and confirmed by HPLC analysis as described previously (Juarez del Valle et al. 2014).

A reference method, the *Lactobacillus delbrueckii* $B_{12}$ assay (Horwitz 2000), was used to prepare cells extracts and, then, to analyze production of cobalamin.

The PS7 strain was able to grow in absence and produce vitamins $B_2$. The concentrations (mean±SD) of intracellular and extracellular riboflavin were 165.00±0.52 and 34.74±3.06 ng/ml, respectively (total concentration: —200 ng/ml). The strain did not produce neither vitamin $B_6$ nor cianocobalamin.

1.10. Adherence to Porcine Mucin

The adhesion of the strain to mucin was determined according to the method described by Cohen and Laux (1995) with some modifications. Briefly, 100 µl of a solution (1 mg/ml) of porcine mucin (Sigma) in HEPES-buffered Hanks salt solution (HH) were immobilized in polystyrene microtiter plates (Maxisorp; Nunc, Roskilde, Denmark) after overnight incubation at 4° C. The wells were washed twice with 250 µl of HH. Parallel, bacteria were grown overnight at 37° C. in MRS broth and the bacterial pellets from 1 ml fractions were obtained by centrifugation and washed with HH. Then, 10 µl of 10 mM carboxyfluorescein (Sigma) were added to the pellets and the bacterial suspensions were incubated for 20 min at 37° C. Subsequently, the bacterial cells were washed 3 times with HH and, finally, resuspended in 1 ml of HH. Then, a suspension of 50 µl of the fluorescent-labelled bacteria (~$5 \times 10^7$ CFU) was added to each well. After incubation for 1 h at 37° C., the plates were washed twice with 250 µl of HH to remove unattached cells, and incubated for 1 h at 60° C. in the presence of 50 µl of 1% sodium dodecyl sulphate (SDS)-0.1 M NaOH to release and lyse bound microorganisms. Fluorescence was measured in a fluorescence microplate reader (Tecan Austria GMBH, Salzburg, Austria). Adhesion was assessed as the percentage of the fluorescence retained in the wells after the washing steps when compared to that present in the labelled bacterial aliquots originally added to the wells. The assays were performed in duplicate.

The PS7 strain showed a high ability to adhere to mucin.

1.11. Degradation of Mucin

The potential of the strain to degrade gastric mucine (HGM; Sigma) in vitro was evaluated in duplicate following the procedure developed by Ruseler-van Embeden et al. (1995) and modified by Zhou et al. (2001).

The PS7 strain was not able to degrade gastric mucin in vitro.

1.12. Antibiogram

The MIC of the 16 antibiotics included in this study was determined on *L. salivarius* PS7 cultures grown overnight in lactic acid bacteria susceptibility test medium (LSM) (Klare et al. 2005) and diluted to obtain a density corresponding to McFarland standard 1 (spectrophotometric equivalent ~$3 \times 10^8$ CFU/ml). The suspension was further adjusted to $3 \times 10^5$ CFU/ml with LSM, and 100 μl were inoculated to wells of microtiter VetMIC plates for lactic acid bacteria (National Veterinary Institute of Sweden, Uppsala, Sweden). The plates were incubated at 37° C. for 48 h and the MIC was defined as the lowest concentration at which no growth was observed.

Parallel, minimum inhibitory concentrations (MICs) were also determined by the E-test (AB BIODISK, Solna, Sweden) following the instructions of the manufacturer. Briefly, after overnight incubation, agar cultures were checked for purity. For inoculums preparation, individual colonies were suspended in a sterile glass culture tube containing 5 ml sterile saline (0.85% NaCl solution) until a density corresponding to a McFarland (McF) standard of 0.5 was obtained. A sterile cotton swab was dipped into the standardized inoculum and used to inoculate an agar plate. Inoculated plates were allowed to dry for approximately 15 min before application of the E-test strips with preformed antimicrobial gradients. After 24 h of incubation, the MIC was defined as the value corresponding to the first point on the E-test strip where growth did not occur along the inhibition ellipse. For bacteriostatic agents (e.g., tetracycline, erythromycin and clindamycin), the MIC was read at the point where growth was inhibited by 80% (i.e., the first point of significant inhibition as judged by the naked eye).

Results from the different antibiotic susceptibility tests were interpreted according to the cut-off levels proposed by the European Food Safety Authority (EFSA, 2012). According to these values, the *Lactobacillus* was sensitive to all the antibiotics tested in this study with the exception of kanamycin and vancomycin (a fact that was expected since all the strains of the *L. salivarius* species are intrinsically resistant to these two antibiotics) (Table 3).

TABLE 3

Minimum inhibitory concentrations (MICs) and cut-off values (μg/ml) of antibiotics against *L. salivarius* PS7.

| Antibiotics | Cut-off values* | MICs (*L. salivarius* PS7) |
|---|---|---|
| Ampicillin | 4 | 0.5 |
| Clindamycin | 1 | 0.5 |
| Chloramphenicol | 4 | 2.0 |
| Erythromycin | 1 | 0.12 |
| Streptomycin | 64 | 32 |
| Gentamicin | 16 | 0.12 |
| Kanamycin | 64 | 128 |
| Tetracyclin | 8 | 2 |
| Vancomycin | n.r. | >128 |

TABLE 3-continued

Minimum inhibitory concentrations (MICs) and cut-off values (μg/ml) of antibiotics against *L. salivarius* PS7.

| Antibiotics | Cut-off values* | MICs (*L. salivarius* PS7) |
|---|---|---|
| Linezolid | 2 | 1 |
| Penicillin | 1 | 0.25 |

*EFSA (2012); Klare et al. (2007) for linezolid and penicillin.
n.r.: nor required 1.13. Formation of Biogenic Amines The ability to form biogenic amines (tyramine, histamine, putrescine and cadaverine) was assessed using the decarboxylase broth and the method described by Bover-Cid and Holzapfel (1999) and, also, by gas chromatography-mass spectrometry. The precursor amino acids (tyrosine, histidine, ornithine and lysine, respectively) were purchased from Sigma.

The PS7 strain was not able to produce biogenic amines.

1.14. Stimulation of Immature Dendritic Cells

Mouse immature dendritic cells (DC) were isolated from the spleen of female C57BL/6 mice (6-10 wk age) and characterized as described previously (Lu et al. 1995). For propagation of isolated DC, they were routinely cultured at 37° C. in a humidified 5% $CO_2$ atmosphere in IMDM medium with 10% heat-inactivated FBS, 2 mM L-glutamine, 100 IU/ml penicillin G, 100 μg/ml streptomycin, and 20 μM β-mercaptoethanol (complete IMDM; all the components were from Sigma) and supplemented with 0.4 ng/ml mouse rGM-CSF (R&D Systems). The culture medium was changed every four days and granulocytes and mature DCs were removed by gentle washes, after which the cultures were replenished with new medium containing fresh rGM-CSF (Lu et al. 1995).

The monoclonal anti-mouse antibodies IA/Ed (2G9) and CD86/B7.2 (GL1), which specifically recognise mouse MHC II and B7.2, respectively, were purchased from PharMingen (San Diego, US). Phycoerythrin and streptavidin were obtained from Sigma.

MRS-Cys overnight cultures of *L. salivarius* PS7 were recovered by centrifugation at 6,000×g for 5 min, and washed twice with PBS. Then, $2 \times 10^7$ cfu were distributed in 100 μl aliquots of Isocove's modified Dulbecco's medium (IMDM) devoid of antibiotics and added to 10 ml fresh DC cultures containing $2 \times 10^6$ cells. The cocultures were incubated for 90 min at 37° C. and non-inoculated DC cultures were included as negative controls. After the incubation period, cells were washed with PBS and 2 mM EDTA and maintained for 18 h at 37° C. in complete IMDM supplemented with gentamicin (250 μg/ml) and tetracycline (10 μg/ml) to kill the remaining bacteria. Then, cells were washed twice with PBS and stained with the anti-MHC class II and anti-B7.2 antibodies in order to detect both DC and the potential activation of the surface markers. Staining was performed according to standard immunofluorescence techniques while labelling of the antibodies with phycoerythrin was carried out following the manufacturer instructions (Sigma). Finally, flow cytometry analysis was performed with a FACS scan (Becton Dickinson, San Jose, CA) and the resulting data were analyzed with the WinMDI 2.8 software. A total of 10,000 cells were analyzed through a viable cell gate determined by forward and right angle light scatter parameters to exclude subcellular particles (Langa et al., 2013).

DC phenotypical changes related to the potential stimulatory action of *L. salivarius* CECT 5713 were evaluated.

After incubation of the bacteria-DC co-cultures (ratio 10:1) for 90 min, the morphology of the DC cells changed dramatically. They became more irregular with visible prolongations or dendrites, which are main features of activated DCs. These morphological changes were observed for at least 24 h after exposure to the bacterial cells. In addition, the lactobacilli strongly enhanced presentation of the coestimulatory molecule B7.2 (CD86) and MHC class II on the surfaces of DC. These markers were detected in 66.2 and 68.9%, respectively, of the co-cultured DC. In contrast, the values corresponding to DC that were not exposed to the bacterial strains were significantly lower (10.7 and 8.8%, respectively).

1.15. Stability after Freeze Drying

*L. salivarius* PS7 was cultivated in MRS broth at 37° C. in aerobiosis. The cells were collected from stationary phase cultures by centrifugation at 10,000×g for 10 min at 4° C. The bacterial pellets were resuspended in reconstituted skim milk (10% p/v) at a final concentration ranging from $10^9$ to $10^{10}$ CFU/ml. The bacterial suspensions were frozen at −80° C. and, subsequently, freeze-dried under the following conditions: 2 h at −20° C., 20 h at −15° C. and, finally, 24 h at 15° C. The freeze-dried cultures were stored at room temperature (~25° C.) and at 4° C. and their viability was checked monthly for an 8 months period.

There were not differences regarding live bacterial counts between initial fresh cultures (9.3-8.8 $\log_{10}$ cfu/g) and freeze-dried cultures (9.3-8.7 $\log_{10}$ cfu/g), immediately after lyophilization process. Then, stability of freeze-dried *L. salivarius* PS7 cultures during storage at room temperature or at 4° C., was checked monthly for 8 months (see FIGS. 2 and 3, respectively; red dots/lines). The count of *L. salivarius* PS7 viable cells were ~8.0-8.6 lop) cfu/g after 3-4 months at room temperature. Viability dropped sharply after 5 months under such conditions. In contrast, the viability was still ~6.8 log $\log_{10}$ cfu/g after 8 months at 4° C.

Example 2: Animal Toxicity Assays 2.1. Acute and Repeated Dose (4-Weeks) Oral Toxicity Studies Wistar male and female rats (Charles River Inc., Marget, Kent, UK) were acclimated for 7 days prior to study initiation with an evaluation of health status. The rats were individually housed in polycarbonate cages with sawdust bedding and maintained in environmentally controlled rooms (22±2° C. and 50%±10% relative humidity) with a 12 h light—dark cycle (light from 08.00 to 20.00 h). Food (A03 rodent diet, Scientific Animal Food and Engineering, Villemoisson-sur-Orge, France) and water were available ad libitum. The rats were 56-days old at the initiation of treatment. Acute (limit test) and repeated dose (4 weeks) studies were conducted in accordance with the European Union guidelines (EC Council Regulation No. 440, 2008a, b). Both studies were undertaken in accordance with the ethics requirements and authorized by the Official Ethical Committee of the Complutense University.

In the acute (limit test) study, 24 rats (12 males, 12 females) were distributed into two groups of 6 males and 6 females each. After an overnight fast each rat received skim milk (500 µl) orally (control group or Group 1), or a single oral dose of $1\times10^{10}$ colony-forming units (cfu) of *L. salivarius* PS7 dissolved in 500 µl of skim milk (treated group or Group 2). Doses of the test and control articles were administered by gavage. Animals were checked for clinical signs and mortality twice a day (a.m. and p.m.). At the end of a 14 days observation period, the rats were weighed, euthanized by $CO_2$ inhalation, exsanguinated, and necropsied.

The repeated dose (4 weeks) (limit test) study was conducted in 48 rats (24 males, 24 females) divided in four groups of 6 males and 6 females each (control group or Group 3; treated group or Group 4; satellite control group or Group 5; and satellite treated group or Group 6). Rats received a daily dose of either skim milk (Groups 3 and 5) or $1\times10^9$ cfu of *L. salivarius* PS7 dissolved in 500 µl of skim milk (Groups 4 and 6) orally once a day over 4 weeks. Doses of the test and control articles were administered by gavage. Animals were dosed at approximately the same time each day (approximately 4-6 h into light cycle). Food but not water was withheld from 4 h before until 2 h after control and test article administration. Animals were checked for clinical signs and mortality twice a day (a.m. and p.m.). All rats of the Groups 3 and 4 were deprived of food for 18 h, weighed, euthanized by $CO_2$ inhalation, exsanguinated, and necropsied on Day 29. All animals of the satellite groups (Groups 5 and 6) were kept a further 14 days without treatment to detect delayed occurrence, or persistence of, or recovery from toxic effects. All rats of the Groups 5 and 6 were deprived of food for 18 h, weighed, euthanized by $CO_2$ inhalation, exsanguinated, and necropsied on day 42.

2.2. Observations

All animals were observed twice daily for general appearance, behaviour, signs of morbidity and mortality (once before treatment and once daily thereafter). Rats were observed for their general condition and the condition of the skin and fur, eyes, nose, oral cavity, abdomen and external genitalia, evaluated for respiration rate and palpated for masses. Behavioural parameters checked were abnormal movements (tremor, convulsion, muscular contractions), reactions to handling and behaviour in open field (excitability, responsiveness to touch and to sharp noise), changes in ordinary behaviour (changes in grooming, head shaking, gyration), abnormal behaviour (autophagia, backward motion) and aggression. Body weight, body weight gain and food and water consumption were measured daily and at the end of the observation periods the rats were examined by necropsy, and the weights of the organs recorded.

2.3. Clinical Test Parameters

Blood samples for haematology and clinical chemistry evaluation were collected from the retro-orbital plexus from animals under light anesthesia induced by $CO_2$ inhalation after 14 days observation period in the acute oral study and alter 4 weeks of treatment and 14 days of recovery for the repeated dose 4 weeks safety study. EDTA was used as an anticoagulant for haematology samples and sodium citrate was used as an anticoagulant for clinical chemistry. Food was withheld for approximately 18 h before blood collection, and samples were collected early in the working day to reduce biological variation; water was provided ad libitum.

Clinical pathology parameters (haematological and clinical biochemistry) were evaluated (Table 4). Most haematology variables were measured with a Coulter/CELL-DYN 3500 whole blood automated analyzer (Abbott, Chicago, IL.). Blood cell smears were observed with an Olympus Microscopy BX41 (Olympus, Tokyo, Japan). Clinical chemistry parameters (Table 1) were evaluated with a spectrophotometer Konelab PRIME 30 (Thermofisher Scientific Inc. Waltham, MA, USA) and special biochemistry parameters with a clinical chemistry analyzer AU640 (Olympus, Tokyo, Japan). Coagulation parameters were analyzed with a coagulation analyzer Coatron M1 (Teco Medical Instruments, GMBH, Neufahrn, Germany).

2.4. Anatomical Pathology

All rats were euthanized by $CO_2$ inhalation and necropsied. The necropsy included a macroscopic examination of the external surface of the body, all orifices, the cranial cavity, the brain and spinal cord, the nasal cavity and paranasal sinuses, and the thoracic, abdominal, and pelvic cavities and viscera. Descriptions of all macroscopic abnormalities were recorded. Samples of the following tissues and organs were collected from all animals at necropsy and fixed in neutral phosphate-buffered 4% formaldehyde solution: adrenal glands, brain, heart, ileum, jejunum, caecum, colon, duodenum, rectum, stomach, oesophagus, trachea, kidneys, liver, lungs, pancreas, spleen, skin, testicles with epididymes, ovaries with oviducts, bone marrow, thymus, thyroid and parathyroid glands, seminal vesicles, urinary bladder and uterus. The organ: body weight ratios were calculated. All organ and tissue samples for histopathological examination were processed, embedded in paraffin, cut at an approximate thickness of 2 to 4μ, and stained with hematoxylin and eosin. Slides of all organs and tissues listed above were collected from all animals of the control and treated groups.

TABLE 4

Haematological and clinical biochemistry parameters.

| (A) Haematological parameters | (B) Clinical biochemistry parameters |
|---|---|
| Red blood cell count (RBC) | Glucose |
| Haemoglobin | Urea |
| Haematocrit | Creatinine |
| Mean corpuscular volume (MCV) | Total protein |
| Mean corpuscular haemoglobin (MCH) | Total bilirubin |
| Mean corpuscular haemoglobin conc. (MCHC) | Calcium |
| Nucleated red blood cell count (RDW) | Sodium |
| White blood cell count (WBC) | Potassium |
| Band neutrophils count | Aspartate aminotransferase (ASAT) |
| Neutrophils count | Alanine aminotranferase (ALAT) |
| Eosinophils count | Alkaline phosphatase |
| Lymphocytes count | Triglyceride |
| Monocytes count | Cholesterol |
| Basophils count | High density lipoproteins (HDL) |
| Platelet count | Low density lipoproteins (LDL) |
| Mean platelet volume (MPV) | Albumine (28 days) |
| Prothrombin time (28 days) | Lipoprotein A (28 days) |
| Thromboplastin partial time (28 days) | |
| Fibrinogen (28 days) | |

2.5. Bacterial Translocation

Bacterial translocation was analysed in blood, liver and spleen. blood (50 μl) were cultured in de Man, Rogosa, Sharpe (MRS) agar medium and incubated at 37° C. during 48 h anaerobically. Tissue samples were homogenized in buffered peptone water (1 g/ml) and 100 μl of the resulting homogenates were cultured on MRS agar as previously mentioned. After 48 h, the plates were checked for the presence of lactobacilli. Positive growth on MRS agar plates was defined by the presence of even a single colony.

2.6. Total Liver Glutathione (GSH) Concentration

A portion of 100 mg of liver from each mouse were homogenized in a 7.5% trichloroacetic acid solution and homogenates were centrifuged at 3,000×g for 10 min at 4° C. Total glutathione concentration was measured in the supernatants using a colorimetric commercial kit (OxisResearch, Portland, OR). Briefly, 40 μl of the homogenates or the standards were added to each well of a microtiter plate, together with 40 ml of a reducing agent (tris(2-carboxyethyl) phosphine in HCl), 40 ml of a chromogen (1-methyl-3-chloro-7-trifluoromethylquinolinium methylsulfate in HCl) and 40 ml of color developer (NaOH). After an incubation at room temperature and in the dark for 30 min, optical density was measured at 415 nm using a microplate spectrophotometer (Bio-Rad Laboratories, Hercules CA).

2.7. Statistical Analysis (Toxicity Studies)

All data are expressed as means±standard error of the mean (SEM) of 6 determinations (i.e. 6 males and 6 females). Differences between control and treated groups were evaluated with a one-way analysis of variance (ANOVA) followed by Dunnett's test (1995), and differences were considered significant at $P<0.05$.

Results

Acute Oral Toxicity in Rats

No abnormal clinical signs, behavioural changes, body weight changes, macroscopic findings, or organ weight changes were observed. All animals survived the 2-week observation period. There were no statistical differences in body weights among groups. Similarly, no statistically significant differences in body weight gain, food and water consumption were noted. Body weight, daily body weight gain, food and water consumption thus were unaffected by the treatment (single oral dose of $1\times10^{10}$ cfu of L. salivarius PS7).

The haematological and clinical chemistry parameters assessed 2 weeks after administration of the strain as a single oral dose of $1\times10^{10}$ cfu were not significantly different compared with those of controls. No treatment-related changes were noted.

There were no statistical differences in organ weight or tissue: body weight ratios related to the test strain (data not shown). The L. salivarius PS7 preparation was not associated with any incidence of macroscopic and microscopic changes. No treatment-related histopathological changes were observed 2 weeks after administration of the strain as a single oral dose of $1\times10^{10}$ cfu. Therefore, L. salivarius PS7 has a low order of acute toxicity and the oral lethal dose (LD50) for male and female rats is higher than $1\times10^{10}$ cfu.

Repeated Dose (4 Weeks) Oral Toxicity in Rats

No mortality was observed. No treatment-related changes in the general condition and external appearance were observed in male and female rats treated with $1\times10^9$ cfu of L. salivarius PS7 daily dose. The development of the animals during the experimental period corresponded to their species and age. There was no significant difference in body weight or body weight gain among groups treated with L. salivarius PS7 in comparison to the control groups at any time point of the experimental period. All L. salivarius PS7-treated groups consumed similar amounts of food and water (data not shown) to that of the corresponding control groups.

All haematology data were within normal limits and differences between groups were no observed. Clinical chemistry data showed no treatment-related alterations at the end of 4-weeks treatment period. Individual values and group mean values were within the physiologic ranges. After 14 days without treatment to detect delayed occurrence of potential toxic effects, there were no treatment-related changes in haematological and clinical test parameters.

The necropsy performed on day 29 after the last dose of L. salivarius PS7 (Group 4) and on day 42 after 14 days without any treatment (Group 6) did not reveal any gross pathological changes or any differences in organ weights in comparison to the corresponding control groups. After 4-weeks of treatment, there were no histopathological findings in the organs examined considered to be treatment related in male and female rats. There were also no treatment-related histopathological findings in the satellite treated group (Group 6).

The no-observed-adverse-effect level in this repeated dose (4 weeks) oral toxicity study was the dose tested, i.e. $1 \times 10^9$ cfu of *L. salivarius* PS7.

Total Liver Glutathione (GSH) Concentration

In order to determine changes in the antioxidant defence because of the probiotic treatment, liver GSH concentration was determined. No significant differences in liver GSH concentration were observed between control and treated groups ($9.67 \pm 1.42$ vs $9.71 \pm 1.56$ mmol/g, $P>0.1$). This indicates that treatment with *L. salivarius* PS7 did not cause oxidative stress to rats and is consistent with the absence of bacteraemia since no lactobacilli could be isolated from blood, liver or spleen of the rats. It suggests that the tested strain do not cause either local or systemic infections in rats.

Example 3: Treatment and Prevention of Otitis in Children 3.1. Subjects

Otitis-prone children (n=64) aged 10 months to 6 years were recruited (their parents were mainly university professors, CSIC scientists or health-related professionals). The inclusion criteria were at least four episodes of AOM during the preceding 12 months, or at least three episodes during the preceding 6 months (del Castillo et al., 2012). Children on regular medication, with chronic illnesses, Down's syndrome, lip or palatal cleft, or who were already scheduled for tympanostomy or adenoidectomy during the study were excluded. Those who had undergone tympanostomy or adenoidectomy during the preceding 6 months were also excluded, unless they had suffered at least three episodes of AOM since the operations. The parents signed their informed consent after receiving information about the study.

3.2. Intervention with *L. Salivarius* PS7

This study was carried out between September 2012 and April 2015. During the 6-month intervention the children consumed daily ~$1 \times 10^9$ cfu of the probiotic bacteria *L. salivarius* PS7. The parents were instructed preferably to open the sachet and empty the powder into milk or a milk product. Parents recorded daily in a study diary whether the child had received the daily doses. The compliance (%) was counted as the number of doses actually received by the children divided by the number of follow-up days. The use of antibiotics (with the exception of the treatment of a AOM episode) or other products containing probiotic bacteria was exclusion criteria during the study.

The primary outcome variables were the occurrence and the duration of AOM episodes. The secondary endpoints were the frequency of pathogen carriage in the external auditory canal.

3.3. Clinical Examinations

At baseline, background information on the child's health, nutrition, living environment and history of otitis/respiratory illnesses was collected by a questionnaire filled in by the parents. The children were examined by a senior physician at baseline, in the middle (3 months), and at the end (6 months) of the study. During these "health visits", which were scheduled at times when the child was free of symptoms of AOM, a general physical examination and a pneumatic otoscopy were performed, and a external auditory canal sample for the bacterial analysis was taken.

The parents were instructed to bring their child to their respective physicians every time they suspected AOM. AOM was diagnosed according to defined clinical criteria, when evidence of middle ear effusion, abnormalities of the tympanic membrane indicating an inflammation, and at least one symptom of an acute infection (fever, ear ache, otorrhoea, etc.), were noted simultaneously. The presence of middle ear effusion was detected in pneumatic otoscopy. The duration of AOM episode was defined based on the duration of existing symptoms after AOM diagnosis Amoxicillin was the first-line antibiotic for the treatment of AOM.

3.4. Microbiological Methods

The microbiota of external auditory canal samples was quantitatively (density) and qualitatively assessed. Samples were taken from the canal with a medium-free swab. Then, 1 ml of peptone water was added and the swab, which was vortexed. The resuspended was inoculated on different agar media (including Columbia CNA and chocolate agar plates). The plates were incubated for up to 48 h, either in aerobiosis or in 5% $CO_2$, at 37° C. The number and morphology of the bacterial colonies were recorded and, at least, one representative of each colony morphology was identified by MALDI-TOF analysis using a Vitek-MS™ instrument (BioMérieux, Marcy l'Etoile, France) in the facilities of Probisearch (Tres Cantos, Spain). Identification was defined as a 99-100% match to the species-specific m/z values in the database.

Results

A total of 64 children who fulfilled the inclusion criteria were enrolled and received the probiotic treatment. Three children (~4.6%) dropped out (one due to antibiotic intake; one due to tympanostomy; one due to allergy to cow's milk protein); thus 62 children completed the study. Compliance during the study was excellent: the percentage of doses ingested by the children was ≥96%.

At least one episode of AOM was diagnosed in 36% of the children. It is interesting to note that such a percentage was notably lower from the 65-72% reported among the otitis-prone children that were attended by the same physicians in the same period and that did not receive the probiotic strain. The percentage is also much lower than that observed in previous studies with other probiotic strains, such as *L. rhamnosus* GG (Hatakka et al., 2007; Tapiovaara et al., 2014). The number of AOM episodes during the 6-month intervention compared to the 6-month period before the intervention decreased in 86%.

When AOM occurred, the median duration of AOM episodes was 3.2 days, which is also much lower compared with non-treated children (6.0 days) or with the results obtained in previous probiotic trials (5.6 days). The number of antimicrobial treatments decreased>60% in the children receiving the probiotic with respect to other otitis-prone children attending the same physicians. The number of episodes of other upper respiratory tract infections was <2.0 among the children receiving the probiotic (compared to >4.6 in the rest of the children).

Globally, the microbial density in the external auditory canal decreased notably along the intervention period, from ≥3 $\log_{10}$ cfu at time 0 (all the cultures were positive at this sampling time) to ≤2 $\log_{10}$ cfu at the end of the intervention (with 29% of the cultures being negative). More specifically, the prevalence of *Haemophilus influenzae*, *Streptococcus pneumoniae*, *Streptococcus pyogenes*, *Moraxella catharralis*, *Alloiococcus otitis*, *Actinomyces europaeus*, *Staphylococcus aureus* and/or *Pseudomonas aeruginosa* was drastically reduced (or disappeared) in the participating children.

REFERENCES

Bover-Cid S & Holzapfel W H 1999 Improved screening procedure for biogenic amine production by lactic acid bacteria. *International Journal of Food Microbiology* 53 33-41.

Brook I, Gober A E 2000. In vitro bacterial interference in the nasopharynx of otitis media-prone and non-otitis media-prone children. *Arch Otolaryngol Head Neck Surg,* 126: 1011-1013.

Çataloluk O. 2001. Molecular characterization of the gene encoding for the salivaricin B activity and its flanking sequences. *Turk J Biol;* 25: 379-386.

Coconnier M H, Klaenhammer T R, Kernéis S., Bernet M F & Servin A L. 1992 Protein-mediated adhesion of *Lactobacillus acidophilus* BG2FO4 on human enterocyte and mucus-secreting cell lines in culture. *Appl Environ Microbiol.* 58 2034-2039.

Cohen P S & Laux D C 1995 Bacterial adhesion to and penetration of intestinal mucus in vitro. *Methods in Enzymology* 253 309-314.

Conway P L, Gorbach S L & Goldin B R 1987 Survival of lactic acid bacteria in the human stomach and adhesion to intestinal cells. *Journal of Dairy Science* 70 1-12.

Del Castillo F, Baquero F, de la Calle, López M V, Ruiz-Canela J, Alfayate S, Moraga F, Cilleruelo M J, Calvo C. 2012. Documento de consenso sobre etiologia, diagnóstico y tratamiento de la otitis media aguda. *Rev Pediatr Aten Primaria* 14: 195-205.

EFSA. 2012. Guidance on the assessment of bacterial susceptibility to antimicrobials of human and veterinary importance. EFSA Panel on Additives and Products or Substances used in Animal Feed (FEEDAP). *EFSA J.* 10: 2740.

Flynn S, van Sinderen D, Thornton G M, Holo H, Nes I F, Collins J K 2002. Characterization of the genetic locus responsible for the production of ABP-118, a novel bacteriocin produced by the probiotic bacterium *Lactobacillus salivarius* subsp. *salivarius* UCC118. *Microbiology* 148: 973-984.

Hatakka K, Blomgren K, Pohjavuori S, Kaijalainen T, Poussa T, Leinonen M, Korpela R, Pitkäranta A. 2007 Treatment of acute otitis media with probiotics in otitis-prone children—a double-blind, placebo-controlled randomised study. *Clin Nutr.* 26: 314-21.

Hendley J O 2002 Clinical practice. Otitis media. *N Engl J Med,* 347: 1169-1174.

Horwitz W 2000. *Official Methods of Analysis of AOAC International.* AOAC International, Gaithersburg.

Juarez del Valle M, Laiño J, Savoy de Giori G, LeBlanc J G 2014. Use of lactic acid bacteria as a biotechnological strategy to increase riboflavin levels in soymilk. *Food Res Int* 62: 1015-1019.

Klare I, Konstabel C, Müller-Bertling S, Reissbrodt R, Huys G, Vancanneyt M, Swings J, Goossens H & Witte W 2005 Evaluation of new broth media for microdilution antibiotic susceptibility testing of lactobacilli, pediococci, lactococci, and bifidobacteria. *Applied and Environmental Microbiology* 71 8982-8986.

Klare I, Konstabel C, Werner G, Huys G, Vankerckhoven V, Kahlmeter G, Hildebrandt B, Müller-Bertling S, Witte W & Goossens H 2007 Antimicrobial susceptibilities of *Lactobacillus, Pediococcus* and *Lactococcus* human isolates and cultures intended for probiotic or nutritional use. *Journal of Antimicrobial Chemotherapy* 59 900-912.

Klein J O. 2001. The burden of otitis media. *Vaccine,* 19 (Suppl 1): S2-S8.

Kullen M J, Sanozky-Dawes R B, Crowell D C & Klaenhammer T R 2000 Use of DNA sequence of variable regions of the 16SrRNA gene for rapid and accurate identification of bacteria in the *Lactobacillus acidophilus* complex. *Journal of Applied Microbiology* 89 511-518.

Laiño, J. E., LeBlanc, J. G., Savoy de Giori 2012 Selection of folate producing starter cultures of yogurt isolated from Northwestern Argentina. *Canadian Journal of Microbiology* 58: 581-588.

Langa S, Maldonado A, Delgado S, et al. 2012. Characterization of *Lactobacillus salivarius* CECT 5713, a strain isolated from human milk: from genotype to phenotype. *Appl Microbiol Biotechnol;* 94:1279-87.

Lu L, Hsieh M, Oriss T B, Morelf P A, Starzl T E, Rao A S, Thomson A W 1995 Generation of D C from mouse spleen cell cultures in response to G M-CSF: immunophenotypic and functional analyses. Immunology 84:127-134

Magnusson J & Schnürer J 2001 *Lactobacillus coryniformis* subsp. *coryniformis* strain Si3 produces a broad-spectrum proteinaceous antifungal compound. *Applied and Environmental Microbiology* 67 1-5.

Marteau P, Minekus M, Havenaar R & Huis In't Veld J H J 1997 Survival of lactic acid bacteria in a dynamic model of the stomach and small intestine: validation and the effects of bile. *Journal of Dairy Science* 80 1031-1037.

Martín R, Olivares M, Marín M L, Xaus J, Fernández L & Rodríguez J M 2005 Characterization of a reuterin-producing *Lactobacillus coryniformis* strain isolated from a goat's milk cheese. *International Journal of Food Microbiology* 104 267-277.

Martín R, Jiménez E, Olivares M, Marín M L, Fernández L, Xaus J & Rodríguez J M. 2006. *Lactobacillus salivarius* CECT 5713, a potential probiotic strain isolated from infant feces and breast milk of a mother-child pair. *Int J Food Microbiol* 112: 35-43.

Niittynen L, Pitkäranta A, Korpela R. 2012 Probiotics and otitis media in children. *Int J Pediatr Otorhinolaryngol.* 2012; 76: 465-70.

Pichichero M E 2000. Recurrent and persistent otitis media. *Pediatr Infect Dis J,* 19: 911-916.

Popova M, Molimard P, Courau S, Crociani J, Dufour C, Le Vacon F, Carton T. 2012 Beneficial effects of probiotics in upper respiratory tract infections and their mechanical actions to antagonize pathogens. *J Appl Microbiol.;* 113: 1305-18.

Reid, G., McGroarty, J. A., Gil Domingue, P. A., Chow, A. W., Bruce, A. W., Eisen, A. and Costerton, J. W. 1990. Coaggregation of urogenital bacterial in vitro and in vivo. *Current Microbiology* 20: 47-52.

Ruiz-Barba J L, Maldonado A & Jiménez-Díaz R 2005 Small-scale total DNA extraction from bacteria and yeast for PCR applications. *Analytical Biochemistry* 347 333-335.

Ruseler-van Embeden J G H, Lieshcut-van L M C, Gosselink M J & Marteau P 1995 Inability of *Lactobacillus casei* strain GG, *L. acidophilus* and *Bifidobacterium bifidum* to degrade intestinal mucus glycoproteins. *Scandinavian Journal of Gastroenterology* 30 675-680.

Tapiovaara L, Lehtoranta L, Swanljung E, Mäkivuokko H, Laakso S, Roivainen M, Korpela R, Pitkäranta A. 2014 *Lactobacillus rhamnosus* G G in the middle ear after randomized, double-blind, placebo-controlled oral administration. *Int J Pediatr Otorhinolaryngol.;* 78:1637-41.

Yap, P. S., Gilliland, S. E. 2000. Comparison of newly isolated strains of *Lactobacillus delbrueckii* susp. *lactis* for hydrogen peroxide production at 5° C. *J. Dairy Sci.* 83, 628-632.

Younes, J. A., van der Mei, H. C., van den Heuvel, E., Busscher, H. J., and Reid. G. (2012). Adhesion forces and coaggregation between vaginal staphylococci and lactobacilli. *PLoS One* 7(5): e36917.

Zhou J S, Gopal P K & Hill H S 2001 Potential probiotic lactic acid bacteria *Lactobacillus rhamnosus* (HN001), *Lactobacillus acidophilus* (HN017) and *Bifidobacterium lactis* (HN019) do not degrade gastric mucin in vitro. *International Journal of Food Microbiology* 63 81-90.

The invention claimed is:

1. A pharmaceutical product comprising an effective amount of a strain of *Lactobacillus salivarius* PS7, and one or more pharmaceutically acceptable excipients selected from the group consisting of glucose, lactose, sucrose, mannitol, maltodextrin, (resistant) starch, cellulose, methylcellulose, magnesium stearate, stearic acid, sodium saccharin, talcum, and magnesium carbonate, wherein the strain *Lactobacillus salivarius* PS7 is deposited under accession number CECT9422.

2. An edible product comprising an effective amount of a strain of *Lactobacillus salivarius* PS7 and one or more edible ingredients selected from the group consisting of glucose, lactose, sucrose, mannitol, maltodextrin, (resistant) starch, cellulose, methylcellulose, magnesium stearate, stearic acid, sodium saccharin, talcum, and magnesium carbonate, wherein the strain *Lactobacillus salivarius* PS7 is deposited under accession number CECT9422.

3. The edible product according to claim 2, wherein the edible product is selected from the group consisting of a dietary supplement, a nutraceutical and a dairy product.

4. The pharmaceutical product according to claim 1, wherein the one or more pharmaceutically acceptable excipients selected from the group consisting of maltodextrin, methylcellulose, magnesium stearate, stearic acid, sodium saccharin, talcum, and magnesium carbonate.

5. The edible product according to claim 2, wherein the one or more edible ingredients selected from the group consisting of maltodextrin, methylcellulose, magnesium stearate, stearic acid, sodium saccharin, talcum, and magnesium carbonate.

6. The pharmaceutical product according to claim 1, wherein the strain of *L. salivarius* is in freeze-dried form.

7. The edible product according to claim 2, wherein the strain of *L. salivarius* is in freeze-dried form.

\* \* \* \* \*